United States Patent
Eyre et al.

[11] Patent Number: 5,817,755
[45] Date of Patent: Oct. 6, 1998

[54] SYNTHETIC PEPTIDE ANALOGS OF CROSS-LINKED N-TELOPEPTIDES OF TYPE I COLLAGEN

[75] Inventors: David R. Eyre, Mercer Island; J. Daniel Clemens, Issaquah; Vincent W. Ochs, Shoreline, all of Wash.

[73] Assignees: Washington Research Foundation; Ostex International, Inc., both of Seattle, Wash.

[21] Appl. No.: 807,030

[22] Filed: Feb. 26, 1997

Related U.S. Application Data

[63] Continuation of PCT/US96/07132 May 17, 1996 which is a Continuation-in-part of Ser. No. 446,206, May 19, 1995, Pat. No. 5,750,647.

[51] Int. Cl.$^6$ .............................. C07K 7/00; C07K 7/06; G01N 33/53; G01N 33/531
[52] U.S. Cl. ................... 530/328; 530/356; 435/7.91; 435/7.93
[58] Field of Search ..................... 530/328, 356

[56] References Cited

U.S. PATENT DOCUMENTS

| | | | |
|---|---|---|---|
| 4,973,666 | 11/1990 | Eyre | 530/323 |
| 5,140,103 | 8/1992 | Eyre | 530/327 |
| 5,300,434 | 4/1994 | Eyre | 435/240.2 |
| 5,320,970 | 6/1994 | Eyre | 436/546 |

FOREIGN PATENT DOCUMENTS

| | | |
|---|---|---|
| 0718309A1 | 6/1996 | European Pat. Off. . |
| WO 94/03813 | 2/1994 | WIPO . |
| WO 96/14844 | 7/1994 | WIPO . |
| WO 95/04282 | 2/1995 | WIPO . |
| WO 95/08115 | 3/1995 | WIPO . |
| WO 9612193 | 4/1996 | WIPO . |

OTHER PUBLICATIONS

Bonde, Martin, et al., "Immunoassay for quantifying type I collagen degradation products in urine evaluated," *Clin Chem.*, 40(11):2022–2025, 1994.

Clemens, et al., "Characteristics of a specific immunoassay for bone resorption based on crosslinked N–telopeptides of bone collagen," *Clinical Chemistry*, 39(6):1247–1248, 1993.

Otter, et al., "Conformational analysis of the type II and III collagen α–I chain N–telopeptides by proton–NMR spectroscopy and restrained molecular mechanics calculations," *Chemical Abstracts*, 119:352, 1993.

*Primary Examiner*—Cecilia J. Tsang
*Assistant Examiner*—Michael Borun
*Attorney, Agent, or Firm*—Christensen, O'Connor, Johnson & Kindness PLLC

[57] ABSTRACT

Synthetic linear peptides embodied by Xaa-Tyr-Xaa-Gly-Xaa-Gly-Val-Gly which mimic the epitope recognized by mAb 1H11 (ATCC No. HB 10611) in cross-linked N-telopeptides of type I collagen (NTx).

12 Claims, No Drawings

5,817,755

SYNTHETIC PEPTIDE ANALOGS OF CROSS-LINKED N-TELOPEPTIDES OF TYPE I COLLAGEN

This application is the U.S. continuation of international patent application Ser. No. PCT/US96/07132, filed May 17, 1996, which is a continuation-in-part of U.S. patent application Ser. No. 08/446,206, filed May 19, 1995, now U.S. Pat. No. 5,750,647 and claims priority from the filing dates thereof.

FIELD OF THE INVENTION

This invention relates to immunoassays and provides a synthetic peptide that acts as an immunoreactive analog of the natural cross-linked amino-terminal telopeptide of type I collagen.

BACKGROUND OF THE INVENTION

Cross-linked N-telopeptides of type I collagen (NTx) are excreted in urine as end-products of the process of bone resorption. These metabolites can be measured by immunoassay to provide an accurate and specific index of bone resorption activity, for example, using the monoclonal antibody (mAb) 1H11 produced by hybridoma 1H11 (ATCC No. HB 10611). The epitope recognized by mAb 1H11 is embodied in forms of the excreted cross-linked N-telopeptides that include the collagen α2(I) N-telopeptide sequence Gln-Tyr-Asp-Gly-K-Gly-Val-Gly, together with a linked second telopeptide from either α1(I) or α2(I), wherein K is embodied in the cross-link. The predominant cross-linked NTx metabolite excreted in urine is shown:

Asp—Glu—K—Ser—Thr—Gly—Gly     α1(I)
               |
Gln—Tyr—Asp—Gly—K—Gly—Val—Gly     α2(I)
                |
                K wherein

K
   |
   K
   |
   K is hydroxylysyl pyridinoline or lysyl pyridinoline, and Gln is glutamine (Q) or wholly cyclized pyrrolidone carboxylic acid (5-oxo-2-pyrrolidinebarboxylic acid, i.e., pyroglutamic acid) (J).

Linear peptides synthesized to match the human α1(l) or α2(l) N-telopeptide sequences, and in which K is simply lysine, are respectively not recognized or recognized very weakly by mAb 1H11. WO 91/08478; Hanson et al., *Journal of Bone and Mineral Research*, 7(11):1251–1258, 1992.

The hybridoma cell line that produces the mAb 1H11 was deposited on Nov. 20, 1990, at the American Type Culture Collection (ATCC), 12301 Parklawn Drive, Rockville, Md. 20852, USA, under accession number HB 10611.

SUMMARY OF THE INVENTION

Here we describe synthetic peptides that exhibit strong binding to mAb 1H11. The subject peptides are embodied by: Gln-Tyr-Xaa-Gly-Xaa-Gly-Val-Gly, wherein Gln is pyrrolidone carboxylic acid, wherein residue Xaa in position 2 is Asp, Glu, or other α-amino acid with a negatively charged side chain (R group), and wherein the structure of residue Xaa in position 5 is such that the peptide mimics features of the cross-linked NTx conformation and chemistry such that the peptide binds to mAb 1H11. In a first embodiment, Xaa in position 5 is selected from among Asp, Glu, and other negatively charged amino acids. In a second embodiment, Xaa in position 5 is selected from among Pro, Nva (norvaline), Trp, His, and conservative substitutions therefor that provide the requisite degree of binding to mAb 1H11. In a third embodiment, Xaa in position 5 bears a thiol group, in which case the peptides may dimerize via a cystine bridge. In a fourth embodiment, Xaa in position 5 bears an amino or thiol group that is conjugated to a carrier molecule or insoluble material. These molecular mimics of the cross-linked NTx epitope are conveniently synthesized for use as immunoassay standards, solid-phase coating antigens, immunogens, and other conjugated molecular structures for measuring NTx in biological samples.

DETAILED DESCRIPTION OF THE PREFERRED EMBODIMENT

The invention provides synthetic linear peptides which mimic the epitope recognized by mAb 1H11 in cross-linked NTx. The subject peptides are embodied by the generic formula Gln-Tyr-Xaa-Gly-Xaa-Gly-Val-Gly, wherein Gln is pyrolidone carboxylic acid, residue Xaa in position 3 is negatively charged, and the structure of residue Xaa in position 5 is such that the peptide mimics the NTx conformation and chemistry to the extent that the peptide binds to mAb 1H11. Representative peptides designated by SEQ ID NOS: 1–59 are shown in the Table below, along with their relative binding affinities for mAb 1H11.

Starting with the observation that the synthesized α2(I) N-telopeptide sequence Gln-Tyr-Asp-Gly-Lys-Gly-Val-Gly (SEQ ID NO:9) is a very weak binding partner for mAb 1H11, a series of peptides was synthesized in which certain amino acids were substituted for lysine (Lys). Improved binding to mAb 1H11 was especially evident when the positively charged Lys residue in position 5 was replaced with amino acids having negatively charged side chains, particularly glutamic acid (Glu) (SEQ ID NO:4) and to a lesser degree aspartic acid (Asp) (SEQ ID NOS:3 and 31). For example, the peptide Gln-Tyr-Asp-Gly-Glu-Gly-Val-Gly (synthesized so that Gln is pyroglutamic acid) had a binding affinity for mAb 1H11 comparable to that of the cross-linked NTx antigen. The mAb 1H11 inhibition curves for NTx (derived from either urine or bone) and Gln-Tyr-Asp-Gly-Glu-Gly-Val-Gly are essentially parallel, indicating that the synthetic peptide mimics the natural epitope. Such preferred embodiments of the subject synthetic peptides bind to mAb 1H11 at a substantially equimolar extent as does the cross-linked NTx metabolite (shown above) in antibody inhibition assays.

Available data suggest that the core sequence, Gln-Tyr-Asp-Gly-Glu-Gly-Val-Gly, represents the requisite size for presenting the epitope recognized by mAb 1H11. Substituting Gly—Gly— for the N-terminal Gln- (SEQ ID NO:41), or adding either -Lys or -Gly-Lys- Leu to the C-terminus (SEQ ID NOS:40 and 42), prevents mAb 1H11 binding.

The degrees to which individual amino acids in the core sequence are considered essential for mAb 1H11 epitope binding are as follows. Binding to mAb 1H11 occurs when the N-terminal Gln (position 1) is in the cyclized form, pyrrolidine carboxylic acid (J), as occurs naturally in collagen chains. The core sequence can be formed with pyrrolidone carboxylic acid in position 1 by initially sequencing the core sequence with Glu in position 1, followed by autoclaving the peptide. Autoclaving causes the cyclization of Glu to pyrrolidone carboxylic acid.

The Tyr residue in position 2 is an essential feature, as iodination of Tyr or substitution with Phe (SEQ ID NO:36) in this position blocks mAb 1H11 binding.

The Asp residue in position 3 is also considered important, as substituents that eliminate the negative charge at this position block mAb 1H11 binding (based upon binding studies with NTx of modified structure from animal species other than human). However, the Asp in position 3 may be replaced by Glu (SEQ ID NO:30) or other α-amino acid residue bearing a negatively charged R group.

The Gly residue in position 4 is important, as the conversative substitution of either Val (SEQ ID NO:37) or Ala (SEQ ID NO:27) at this position substantially eliminates mAb 1H11 binding affinity.

The Gly residues at positions 6 and 8 are equally important, as various substitutions at these positions, including Ala, Val, Leu, Pro, and Cys, lead to loss of mAb 1H11 binding affinity. (See SEQ ID NOS:28, 35, 46, 49, 52, 54, and 56.)

The Val residue at position 7 is important, as conservative substitutions of other hydrophobic substituents, such as Leu (SEQ ID NO:29) or Ile (SEQ ID NO:55), eliminate the requisite binding of mAb 1H11.

Accordingly, the invention provides, in a first embodiment, a peptide that binds to mAb 1H11, comprising Gln-Tyr-Xaa-Gly-Xaa-Gly-Val-Gly (SEQ ID NO:60), wherein Gln is pyrrolidone carboxylic acid, Xaa in position 3 is a negatively charged amino acid residue, and Xaa in position 5 is also an amino acid with a negatively charged R group. A suitable amino acid with a negatively charged R group is selected from among Glu, Asp, and other natural and synthetic a-amino acids which bear a negatively charged R group such as a carboxyl, sulfate, or phosphate group. Representative examples include α-aminoadipic acid (SEQ ID NO:34) and cysteic acid (SEQ ID NO:26).

In a second embodiment, the Xaa residue in position 5 is selected from among Pro, Trp, Nva, and His (SEQ ID NO:61) or conservative substitutions therefor that afford a requisite degree of mAb 1H11 binding. Representative amino acids with a nonpolar R group include Pro (SEQ ID NO: 13), Trp (SEQ ID NO: 19), norvaline (SEQ ID NO:38), and other natural and synthetic α-amino acids which bear a nonpolar R group such as characterize Ala, Ile, Leu, Met, Phe, Pro, Trp, and Val.

The substitution of His at position 5 (SEQ ID NO:7) provided a more limited degree of 1H11 binding. Other natural and synthetic α-amino acids bearing positively charged R groups can be conveniently synthesized and tested pursuant to this disclosure.

Among the tested amino acids with a polar but uncharged R group, Cys in position 5 (SEQ ID NO:2) provided excellent binding to mAb 1H11. It is contemplated that other natural and synthetic α-amino acids which bear a polar but uncharged R group such as characterize Asn, Cys, Gln, Gly, Ser, Thr, and Tyr may also be suitable. Representative examples include pyridinylalanine (SEQ ID NO:62) (Bachem) and other α-amino acids wherein the R group has a pyridine ring. Cysteine and other thiol bearing α-amino acids are particularly preferred embodiments in terms of the degree of mAb 1H11 binding.

Thus, in a third embodiment, the invention provides a peptide that binds to mAb 1H11, comprising Gln-Tyr-Xaa-Gly-Xaa-Gly-Val-Gly (SEQ ID NO:63), wherein Gln is pyrrolidone carboxylic acid, Xaa in position 3 is a negatively charged amino acid residue, and Xaa in position 5 is an α-amino acid bearing a thiol group. Representative examples include cysteine (SEQ ID NO:2), homocysteine (SEQ ID NO:64), and related residues in which R contains 0–3 carbon atoms. In the presence of atmospheric oxygen this peptide forms disulfide-bonded dimers that mimic the NTx epitope as follows:

$$\begin{array}{c}\text{Gln—Tyr—Xaa—Gly—Xaa—Gly—Val—Gly}\\|\\S\\|\\S\\|\\\text{Gln—Tyr—Xaa—Gly—Xaa—Gly—Val—Gly.}\end{array}$$

Each of the residues Xaa in position 5 may be the same or a different α-amino acid bearing a side chain (R) with a thiol group.

In a fourth embodiment, the natural epitope embodied in urinary NTx is mimicked by conjugating the synthetic peptide Gln-Tyr-Xaa-Gly-Xaa-Gly-Val-Gly (SEQ ID NO:65) to either a solute or an insoluble material. Here, the Gln and the Xaa in position 3 are as defined above, and the Xaa in position 5 is an α-amino acid bearing a side chain amino or thiol group. For example, Xaa in position 5 may be lysine (SEQ ID NO:9) with an epsilon amino group, in which case conjugation to the solute or insoluble material is through the amino group, for example by glutaraldehyde using standard procedures. Representative Xaa residues for this purpose are lysine and cysteine (SEQ ID NO:2), and representative linking agents, for conjugation to, e.g., bovine serum albumin, are glutaraldehyde and m-malieimidobenzoyl-N-hydroxy-succinimide ester (MBS), respectively. By solute is meant a molecular substance dissolved in aqueous solution. Represenative solutes for this purpose include proteins, such as keyhole limpet hemocyanin (KLH), albumin, and enzymes, peptides such as Gln-Tyr-Asp-Gly-Cys-Gly-Val-Gly (or Gln-Tyr-Asp-Gly-Lys-Gly-Val-Gly), and other soluble molecules such as biotin, avidin, and fluorescent and chemiluminescent moieties. Representative insoluble materials include latex particles, dipsticks, micro-titer wells, and other substrata used in heterogeneous immunoassays. Once conjugated by such a standard linking agent to, for example, KLH, the antibody-binding affinity of the Gln-Tyr-Asp-Gly-Lys-Gly-Val-Gly peptide for mAb 1H11 is increased about 50-fold, approximating the binding affinity of the natural epitope. Such a conjugate can be used in solution as a competing antigen or as a coating agent for solid surfaces, for example, to coat wells in a microtiter-plate kit or latex or other particles in automated assay systems.

Accordingly, this fourth embodiment of the invention provides a conjugated peptide that binds to mAb 1H11, comprising:

$$\begin{array}{c}\text{Gln—Tyr—Xaa—Gly—Xaa—Gly—Val—Gly}\\|\\R\end{array}$$

wherein Gln is pyrrolidone carboxylic acid, Xaa in position 3 is a negatively charged amino acid residue, Xaa in position 5 is an amino acid residue bearing an amino group or thiol group, and R is either a solute or an insoluble material conjugated through the amino group or thiol group to residue Xaa in position 5.

EXAMPLE

Testing synthetic peptides for binding to mAb 1H11.

The synthetic peptides of the present invention are prepared by methods well known in the art, for example as summarized in A. P. Gloor, et al., Synthesis Notes, Novabiochem Catalog and Peptide Synthesis Handbook, La Jolla, Calif., pp. S1–S5, 1994–1995. For the following experiment, synthetic peptides were purchased from an outside vendor, or made in house using the Symphony/Multiplex (TM) multiple peptide synthesizer from Rainin Instrument Co. (Woburn, Mass.)

Less than 10% of the peptides were tested for purity. Those that were examined were found to be greater than 80% pure by reverse phase HPLC.

Most of the peptides made have a single aromatic amino acid, tyrosine. We assumed the extinction coefficient of tyrosine at 280 nanometers to be equal to the extinction coefficient of the synthetic peptides. If the peptides had additional aromatic residues, logical adjustments were made to the extinction coefficient.

Generally, a milligram per mL solution of the peptide was made in PBS. The absorbence at A280 was read and the concentration confirmed. Dilutions of the peptide were then made in a buffer such as OSTEOMARK (TM) calibrator diluent (OSTEOMARK Assay, Ostex International, Seattle, Wash.). Working strength concentrations were between 10 and 0.01 micrograms per milliliter.

To test the apparent affinity of the synthetic peptides for mAb 1H11, the OSTEOMARK assay was run using OSTEOMARK kits and components, including monoclonal antibody 1H11. A standard curve was run using OSTEOMARK calibrators. Peptide samples were generally tested at 10, 3, 1, and down to 0.01 µG per mL. The standard OSTEOMARK curve was generated using a four parameter logistic curve fit program (MedData Inc., N.Y., N.Y.). Peptide values were back fit into the standard curve and values were reported in picomoles Bone Collagen Equivalents (BCE)/mL (which equals nanomolar BCE, or nM BCE). As not all peptides that competed for 1H11 showed a linear response, values between 0.5 and 1 optical density units were taken and averaged.

Representative peptides made and tested are shown in the following Table. Values in the Table are reported as the number of nanomoles of BCE equivalent to a microgram of a given peptide. Antibody binding values below 500 nMole BCE were considered to be commercially insignificant.

TABLE

Synthetic Linear Peptides Alpha 2 chain of type 1 collagen

| SEQ ID NO: | 0 | 1 | 2 | 3 | 4 | 5 | 6 | 7 | 8 | 9 | 10 | 11 | Results[1] |
|---|---|---|---|---|---|---|---|---|---|---|---|---|---|
| 1 | J | Y | D | G | A | G | V | G | | | | | 483 |
| 2 | J | Y | D | G | C | G | V | G | | | | | 2500 |
| 3 | J | Y | D | G | D | G | V | G | | | | | 1840 |
| 4 | J | Y | D | G | E | G | V | G | | | | | 2400 |
| 5 | J | Y | D | G | F | G | V | G | | | | | 365 |
| 6 | J | Y | D | G | G | G | V | G | | | | | 114 |
| 7 | J | Y | D | G | H | G | V | G | | | | | 650 |
| 8 | J | Y | D | G | I | G | V | G | | | | | 250 |
| 9 | J | Y | D | G | K | G | V | G | | | | | 100 |
| 10 | J | Y | D | G | L | G | V | G | | | | | 230 |
| 11 | J | Y | D | G | M | G | V | G | | | | | 183 |
| 12 | J | Y | D | G | N | G | V | G | | | | | 135 |
| 13 | J | Y | D | G | P | G | V | G | | | | | 2056 |
| 14 | J | Y | D | G | Q | G | V | G | | | | | 148 |
| 15 | J | Y | D | G | R | G | V | G | | | | | 23 |
| 16 | J | Y | D | G | S | G | V | G | | | | | 30 |
| 17 | J | Y | D | G | T | G | V | G | | | | | 252 |
| 18 | J | Y | D | G | V | G | V | G | | | | | 400 |
| 19 | J | Y | D | G | W | G | V | G | | | | | 1300 |
| 20 | J | Y | D | G | Y | G | V | G | | | | | 104 |
| 21 | J | Y | D | G | R | G | V | A | | | | | 6 |
| 22 | J | Y | D | G | E | G | V | L | | | | | <50 |
| 23 | J | Y | D | G | E | G | V | | | | | | <50 |
| 24 | J | Y | D | G | E | | | | | | | | <50 |
| 25 | | Y | D | G | E | G | V | | | | | | <50 |
| 26 | j | Y | D | G | X[2] | G | V | G | | | | | 1000 |
| 27 | J | Y | D | A | E | G | V | G | | | | | <50 |
| 28 | J | Y | D | G | E | A | V | G | | | | | <50 |
| 29 | J | Y | D | G | E | G | V | G | | | | | <50 |
| 30 | J | Y | E | G | E | G | V | G | | | | | 3000 |
| 31 | J | Y | D | G | D | G | V | G | | | | | 1400 |
| 32 | J | Y | E | G | D | G | V | G | | | | | 1000 |
| 33 | E[3] | Y | D | G | E | G | V | G | | | | | 2000 |
| 34 | J | Y | D | G | X[4] | G | V | G | | | | | 750 |
| 35 | J | Y | D | G | E | G | V | V | | | | | 5 |
| 36 | J | F | D | G | E | G | V | G | | | | | 14 |
| 37 | J | Y | D | V | E | G | V | G | | | | | 6 |
| 38 | J | Y | D | G | X[5] | G | V | G | | | | | 860 |
| 39 | Q | Y | D | G | E | G | V | G | | | | | <50 |
| 40 | J | Y | D | G | E | G | V | G | L | | | | <50 |
| 41 | G | G | Y | D | G | E | G | V | G | | | | <50 |
| 42 | J | Y | D | G | E | G | V | G | G | K | L | | <50 |
| 43 | S | Y | D | G | E | G | V | G | | | | | <50 |
| 44 | J | Y | D | G | E | G | V | X[6] | | | | | <50 |
| 45 | G | V | G | C | G | D | Y | Q | | | | | <50 |
| 46 | J | Y | D | G | E | V | V | G | | | | | <50 |
| 47 | J | Y | D | G | E | G | G | G | | | | | <50 |
| 48 | J | Y | D | G | E | G | A | G | | | | | <50 |
| 49 | J | Y | D | G | E | G | V | A | | | | | <50 |
| 50 | H | Y | D | G | E | G | V | G | | | | | nd |
| 51 | P | Y | D | G | E | G | V | G | | | | | <50 |
| 52 | J | Y | D | G | E | C | G | G | | | | | <50 |
| 53 | J | V | G | E | G | D | Y | N | | | | | <50 |
| 54 | J | Y | D | G | E | G | V | P | | | | | <50 |
| 55 | J | Y | D | G | E | G | I | G | | | | | <50 |
| 56 | J | Y | D | G | E | G | V | C | | | | | <50 |
| 57 | X[7] | Y | D | G | E | G | V | G | | | | | nd[8] |
| 58 | J | Y | D | G | X[9] | G | V | G | | | | | 135 |
| 59 | J | Y | D | G | X[10] | G | V | G | | | | | nd |

[1] Peptide binding to mAb 1H11 is expressed in the following units: 1µg synthetic peptide = X nmole BCE, where X is the value in the Table. For comparison, the native sequence, JYDGKGVG (SEQ ID NO:9), gave an X value of 100 in this assay.

[2] X = cysteic acid (2-amino-3-sulfopropanoic acid). That is, cysteine with a sulfite ($-SO_3^{-2}$) group substituted for the normal mercapto ($-SH$) group, preventing disulfide bridges.

[3] The sequence EYDGEGVG is not recognized by 1H11. Here, by autoclaving this peptide under conditions that convert the glutamic acid in position 1 into pyroglutamic acid, substantial increase in 1H11 binding resulted. Therefore, the N terminus pyroglutamic acid is part of the epitope.

[4] X = α-aminoadipic acid (2-amino hexanedioic acid), in which the side chain amino group of lysine is replaced by a negatively charged carboxyl group.

[5] X = Norvaline.

[6] X = G—$NH_2$. The carboxyl group of the Gly residue in position 8 is normally exposed (not in peptide bond). Here, an amino group was added to the carboxyl group (to make 1,2-diaminoacetaldehyde), which prevented recognition. Therefore, the free carboxyl group is considered part of the epitope.

[7] X = 4-hydroxyproline.

[8] nd = not determined.

[9] X = Biotinolated lysine (K).

[10] X = Biotinolated cysteine (C).

The embodiments of the invention in which an exclusive property or privilege is claimed are defined as follows:

1. A peptide that binds to the antibody obtainable from ATCC HB 10611, the peptide consisting of:

Gln-Tyr-Xaa-Gly-Xaa-Gly-Val-Gly wherein Gln is pyrrolidone carboxylic acid, Xaa in position 3 is a negatively charged amino acid, and Xaa in position 5 is either a negatively charged amino acid, or is selected from among Pro, Trp, Nva, and His, or is an amino acid bearing a thiol group, or is Xaa-R wherein Xaa is an amino acid bearing an amino or thiol group and R is a solute or insoluble material conjugated through the amino or thiol group to Xaa.

2. The peptide of claim 1, wherein Xaa in position 3 is Glu, Asp, cysteic acid, or α-aminoadipic acid.

3. The peptide of claim 1, wherein Xaa in position 5 is a negatively charged amino acid (SEQ ID NO:60).

4. The peptide of claim 3 wherein Xaa in position 5 is Glu (SEQ ID NO:66), Asp (SEQ ID NO:67), cysteic acid (SEQ ID NO:68), or α-aminoadipic acid (SEQ ID NO:69).

5. The peptide of claim 1, wherein Xaa in position 5 is selected from among Pro (SEQ ID NO:70), Trp (SEQ ID NO:71), Nva (SEQ ID NO:72), and His (SEQ ID NO:73).

6. The peptide of claim 1, wherein Xaa in position 5 is an α-amino acid bearing a thiol group (SEQ ID NO:63).

7. The peptide of claim 6, wherein Xaa in position 5 is cysteine (SEQ ID NO:74) or homocysteine (SEQ ID NO:64).

8. A peptide that binds to the antibody obtainable from ATCC HB 10611, the peptide consisting of:

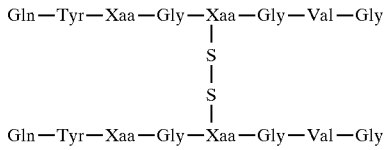

wherein Gln is pyrrolidone carboxylic acid, Xaa in position 3 is a negatively charged amino acid and Xaa in position 5 is an amino acid bearing a thiol group.

9. The dimeric peptide of claim 8, wherein each Xaa in position 5 is independently cysteine or homocysteine.

10. A peptide of claim 1, consisting of:

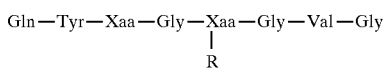

wherein Xaa in position 5 is an amino acid residue bearing an amino or thiol group, and R is a solute conjugated through the amino or thiol group to the Xaa.

11. The peptide of claim 10, wherein the solute is a protein or peptide.
12. The peptide of claim 1, consisting of:
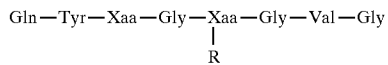
wherein Xaa in position 5 is an amino acid residue bearing an amino or thiol group, and R is an insoluble material conjugated through the amino or thiol group to the Xaa.
* * * * *

UNITED STATES PATENT AND TRADEMARK OFFICE
CERTIFICATE OF CORRECTION

PATENT NO. : 5,817,755
DATED : October 6, 1998
INVENTOR(S) : D.R. Eyre et al.

It is certified that error appears in the above-indentified patent and that said Letters Patent is hereby corrected as shown below:

| COLUMN | LINE | |
|---|---|---|
| Pg. 1, col. 2 | Assistant Examiner Name | "Borun" should read --Borin-- |
| 1 | 48 | "pyrrolidinebarboxylic" should read --pyrrolidinecarboxylic-- |
| 1 | 54 | "*andMineral*" should read --*and Mineral*-- |
| 2 | 56 | "Lys- Leu" should read --Lys-Leu-- |
| 3 | 11-12 | "conversative" should read --conservative-- |
| 3 | 32 | "a-amino" should read --$\alpha$-amino-- |
| 3 | 64 | "Gin" should read --Gln-- |
| 4 | 31 | "Representive" should read --Representative-- |
| 6 | Table, col. 1 line 26 | "j" should read --J-- |
| 6 | Table, col. 7 line 29 | "V" should read --L-- |

UNITED STATES PATENT AND TRADEMARK OFFICE
CERTIFICATE OF CORRECTION

PATENT NO. : 5,817,755
DATED : October 6, 1998
INVENTOR(S) : D.R. Eyre et al.

Page 2 of 3

It is certified that error appears in the above-indentified patent and that said Letters Patent is hereby corrected as shown below:

| COLUMN | LINE | | | |
|---|---|---|---|---|
| 6 | Table lines 58-9 | " 58 J Y D G $X^9$ G V G<br>59 J Y D G $X^{10}$ G V G nd | 135<br>" | | should read:

-- 58 J Y D G $X^9$ G V G     135
   59 J Y D G $X^{10}$ G V G     nd--

| 6 | After Table, before footnotes | please insert the following two paragraphs: |

--In summary, the invention provides synthetic peptides that mimic the complex epitope of cross-linked human bone and urinary NTx recognized immunochemically, for example, by mAb 1H11. These synthetic peptides can be used to simplify the manufacture of immunoassay kits and other commercial formats, so as to provide reproducible standards for calibration and novel synthetic antigen formulations, for use for example in homogeneous immunoassay systems such as disclosed in U.S. Patents No. 5,212,064 and No. 5,362,625 (Microgenics Corporation) and other automated assay systems. Such usage of the subject synthetic peptides as immunoassay standards, solid-phase coating antigens, immunogens, and other conjugated molecular structures for immunoassays follow from conventional information available to those skilled in the art, for

UNITED STATES PATENT AND TRADEMARK OFFICE
CERTIFICATE OF CORRECTION

PATENT NO. : 5,817,755
DATED : October 6, 1998
INVENTOR(S) : D.R. Eyre et al.

It is certified that error appears in the above-indentified patent and that said Letters Patent is hereby corrected as shown below:

COLUMN     LINE

(Continued)     example, as disclosed in: Principles and Practice of Immunoassay, C. P. Price and D. J. Newman (Eds.), Stockton Press, NY, 1991.

While the preferred embodiment of the invention has been illustrated and described, it will be appreciated that various changes can be made therein without departing from the spirit and scope of the invention.--

6     Table (footnote 1, line 2)     "nmole" should read --nMole--

Signed and Sealed this

Thirtieth Day of March, 1999

*Attest:*

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 74

( 2 ) INFORMATION FOR SEQ ID NO:1:

( i ) SEQUENCE CHARACTERISTICS:
( A ) LENGTH: 8 amino acids
( B ) TYPE: amino acid
( C ) STRANDEDNESS:
( D ) TOPOLOGY: linear ( i i ) MOLECULE TYPE: peptide ( v ) FRAGMENT TYPE: N-terminal ( i x ) FEATURE:
( A ) NAME/KEY: misc-feature
( B ) LOCATION: 1
( D ) OTHER INFORMATION: Xaa is pyroglutamic acid ( x i ) SEQUENCE DESCRIPTION: SEQ ID NO:1:

Xaa  Tyr  Asp  Gly  Ala  Gly  Val  Gly
1                    5

( 2 ) INFORMATION FOR SEQ ID NO:2:

( i ) SEQUENCE CHARACTERISTICS:
( A ) LENGTH: 8 amino acids
( B ) TYPE: amino acid
( C ) STRANDEDNESS:
( D ) TOPOLOGY: linear ( i i ) MOLECULE TYPE: peptide ( v ) FRAGMENT TYPE: N-terminal ( i x ) FEATURE:
( A ) NAME/KEY: misc-feature
( B ) LOCATION: 1
( D ) OTHER INFORMATION: Xaa is pyroglutamic acid ( x i ) SEQUENCE DESCRIPTION: SEQ ID NO:2:

Xaa  Tyr  Asp  Gly  Cys  Gly  Val  Gly
1                    5

( 2 ) INFORMATION FOR SEQ ID NO:3:

( i ) SEQUENCE CHARACTERISTICS:
( A ) LENGTH: 8 amino acids
( B ) TYPE: amino acid
( C ) STRANDEDNESS:
( D ) TOPOLOGY: linear ( i i ) MOLECULE TYPE: peptide ( v ) FRAGMENT TYPE: N-terminal ( i x ) FEATURE:
( A ) NAME/KEY: misc-feature
( B ) LOCATION: 1
( D ) OTHER INFORMATION: Xaa is pyroglutamic acid ( x i ) SEQUENCE DESCRIPTION: SEQ ID NO:3:

Xaa  Tyr  Asp  Gly  Asp  Gly  Val  Gly
1                    5

( 2 ) INFORMATION FOR SEQ ID NO:4:

( i ) SEQUENCE CHARACTERISTICS:

(A) LENGTH: 8 amino acids
             (B) TYPE: amino acid
             (C) STRANDEDNESS:
             (D) TOPOLOGY: linear (i i) MOLECULE TYPE: peptide (v) FRAGMENT TYPE: N-terminal (i x) FEATURE:
             (A) NAME/KEY: misc-feature
             (B) LOCATION: 1
             (D) OTHER INFORMATION: Xaa is pyroglutamic acid (x i) SEQUENCE DESCRIPTION: SEQ ID NO:4:

Xaa  Tyr  Asp  Gly  Glu  Gly  Val  Gly
    1                   5

(2) INFORMATION FOR SEQ ID NO:5:

(i) SEQUENCE CHARACTERISTICS:
             (A) LENGTH: 8 amino acids
             (B) TYPE: amino acid
             (C) STRANDEDNESS:
             (D) TOPOLOGY: linear (i i) MOLECULE TYPE: peptide (v) FRAGMENT TYPE: N-terminal (i x) FEATURE:
             (A) NAME/KEY: misc-feature
             (B) LOCATION: 1
             (D) OTHER INFORMATION: Xaa is pyroglutamic acid (x i) SEQUENCE DESCRIPTION: SEQ ID NO:5:

Xaa  Tyr  Asp  Gly  Phe  Gly  Val  Gly
    1                   5

(2) INFORMATION FOR SEQ ID NO:6:

(i) SEQUENCE CHARACTERISTICS:
             (A) LENGTH: 8 amino acids
             (B) TYPE: amino acid
             (C) STRANDEDNESS:
             (D) TOPOLOGY: linear (i i) MOLECULE TYPE: peptide (v) FRAGMENT TYPE: N-terminal (i x) FEATURE:
             (A) NAME/KEY: misc-feature
             (B) LOCATION: 1
             (D) OTHER INFORMATION: Xaa is pyroglutamic acid (x i) SEQUENCE DESCRIPTION: SEQ ID NO:6:

Xaa  Tyr  Asp  Gly  Gly  Gly  Val  Gly
    1                   5

(2) INFORMATION FOR SEQ ID NO:7:

(i) SEQUENCE CHARACTERISTICS:
             (A) LENGTH: 8 amino acids
             (B) TYPE: amino acid
             (C) STRANDEDNESS:
             (D) TOPOLOGY: linear (i i) MOLECULE TYPE: peptide (v) FRAGMENT TYPE: N-terminal (i x) FEATURE:
             (A) NAME/KEY: misc-feature (B) LOCATION: 1
(D) OTHER INFORMATION: Xaa is pyroglutamic acid (xi) SEQUENCE DESCRIPTION: SEQ ID NO:7:

Xaa Tyr Asp Gly His Gly Val Gly
1               5

(2) INFORMATION FOR SEQ ID NO:8:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (v) FRAGMENT TYPE: N-terminal (ix) FEATURE:
(A) NAME/KEY: misc-feature
(B) LOCATION: 1
(D) OTHER INFORMATION: Xaa is pyroglutamic acid (xi) SEQUENCE DESCRIPTION: SEQ ID NO:8:

Xaa Tyr Asp Gly Ile Gly Val Gly
1               5

(2) INFORMATION FOR SEQ ID NO:9:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (v) FRAGMENT TYPE: N-terminal (ix) FEATURE:
(A) NAME/KEY: misc-feature
(B) LOCATION: 1
(D) OTHER INFORMATION: Xaa is pyroglutamic acid
/ note=."alpha2(I) type I collagen"

(xi) SEQUENCE DESCRIPTION: SEQ ID NO:9:

Xaa Tyr Asp Gly Lys Gly Val Gly
1               5

(2) INFORMATION FOR SEQ ID NO:10:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (v) FRAGMENT TYPE: N-terminal (ix) FEATURE:
(A) NAME/KEY: misc-feature
(B) LOCATION: 1
(D) OTHER INFORMATION: Xaa is pyroglutamic acid (xi) SEQUENCE DESCRIPTION: SEQ ID NO:10:

Xaa Tyr Asp Gly Leu Gly Val Gly
1               5

(2) INFORMATION FOR SEQ ID NO:11:

( i ) SEQUENCE CHARACTERISTICS:
  ( A ) LENGTH: 8 amino acids
  ( B ) TYPE: amino acid
  ( C ) STRANDEDNESS:
  ( D ) TOPOLOGY: linear ( i i ) MOLECULE TYPE: peptide ( v ) FRAGMENT TYPE: N-terminal ( i x ) FEATURE:
  ( A ) NAME/KEY: misc-feature
  ( B ) LOCATION: 1
  ( D ) OTHER INFORMATION: Xaa is pyroglutamic acid ( x i ) SEQUENCE DESCRIPTION: SEQ ID NO:11:

Xaa Tyr Asp Gly Met Gly Val Gly
1               5

( 2 ) INFORMATION FOR SEQ ID NO:12:

( i ) SEQUENCE CHARACTERISTICS:
  ( A ) LENGTH: 8 amino acids
  ( B ) TYPE: amino acid
  ( C ) STRANDEDNESS:
  ( D ) TOPOLOGY: linear ( i i ) MOLECULE TYPE: peptide ( v ) FRAGMENT TYPE: N-terminal ( i x ) FEATURE:
  ( A ) NAME/KEY: misc-feature
  ( B ) LOCATION: 1
  ( D ) OTHER INFORMATION: Xaa is pyroglutamic acid ( x i ) SEQUENCE DESCRIPTION: SEQ ID NO:12:

Xaa Tyr Asp Gly Asn Gly Val Gly
1               5

( 2 ) INFORMATION FOR SEQ ID NO:13:

( i ) SEQUENCE CHARACTERISTICS:
  ( A ) LENGTH: 8 amino acids
  ( B ) TYPE: amino acid
  ( C ) STRANDEDNESS:
  ( D ) TOPOLOGY: linear ( i i ) MOLECULE TYPE: peptide ( v ) FRAGMENT TYPE: N-terminal ( i x ) FEATURE:
  ( A ) NAME/KEY: misc-feature
  ( B ) LOCATION: 1
  ( D ) OTHER INFORMATION: Xaa is pyroglutamic acid ( x i ) SEQUENCE DESCRIPTION: SEQ ID NO:13:

Xaa Tyr Asp Gly Pro Gly Val Gly
1               5

( 2 ) INFORMATION FOR SEQ ID NO:14:

( i ) SEQUENCE CHARACTERISTICS:
  ( A ) LENGTH: 8 amino acids
  ( B ) TYPE: amino acid
  ( C ) STRANDEDNESS:
  ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:14:

Xaa Tyr Asp Gly Gln Gly Val Gly
1                 5

( 2 ) INFORMATION FOR SEQ ID NO:15:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:15:

Xaa Tyr Asp Gly Arg Gly Val Gly
1                 5

( 2 ) INFORMATION FOR SEQ ID NO:16:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:16:

Xaa Tyr Asp Gly Ser Gly Val Gly
1                 5

( 2 ) INFORMATION FOR SEQ ID NO:17:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:17:

Xaa Tyr Asp Gly Thr Gly Val Gly
1                 5

( 2 ) INFORMATION FOR SEQ ID NO:18:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:18:

Xaa Tyr Asp Gly Val Gly Val Gly
1                      5

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:19:

Xaa Tyr Asp Gly Trp Gly Val Gly
1                      5

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:20:

Xaa Tyr Asp Gly Tyr Gly Val Gly
1                      5

( 2 ) INFORMATION FOR SEQ ID NO:21:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:21:

Xaa  Tyr  Asp  Gly  Arg  Gly  Val  Ala
1                             5

( 2 ) INFORMATION FOR SEQ ID NO:22:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:22:

Xaa  Tyr  Asp  Gly  Glu  Gly  Val  Leu
1                             5

( 2 ) INFORMATION FOR SEQ ID NO:23:

( i ) SEQUENCE CHARACTERISTICS:
    ( A ) LENGTH: 7 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:23:

Xaa  Tyr  Asp  Gly  Glu  Gly  Val
1                             5

( 2 ) INFORMATION FOR SEQ ID NO:24:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:24:

Xaa  Tyr  Asp  Gly  Glu
1                             5

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:25:

Xaa  Asp  Gly  Glu  Gly  Val
    1                         5

( 2 ) INFORMATION FOR SEQ ID NO:26:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1, 5..6
        ( D ) OTHER INFORMATION: Xaa in position 1 is pyroglutamic
                acid ( i x ) FEATURE:
        ( A ) NAME/KEY: misc-feature
        ( B ) LOCATION: 5
        ( D ) OTHER INFORMATION: Xaa in position 5 is cysteic acid ( x i ) SEQUENCE DESCRIPTION: SEQ ID NO:26:

Xaa  Tyr  Asp  Gly  Xaa  Gly  Val  Gly
    1                         5

( 2 ) INFORMATION FOR SEQ ID NO:27:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:27:

Xaa  Tyr  Asp  Ala  Glu  Gly  Val  Gly
    1                         5

( 2 ) INFORMATION FOR SEQ ID NO:28:

( i ) SEQUENCE CHARACTERISTICS:
        ( A ) LENGTH: 8 amino acids (B) TYPE: amino acid
(C) STRANDEDNESS:
(D) TOPOLOGY: linear (ii) MOLECULE TYPE: peptide (v) FRAGMENT TYPE: N-terminal (ix) FEATURE:
(A) NAME/KEY: misc-feature
(B) LOCATION: 1
(D) OTHER INFORMATION: Xaa is pyroglutamic acid (xi) SEQUENCE DESCRIPTION: SEQ ID NO:28:

Xaa Tyr Asp Gly Glu Ala Val Gly
1               5

(2) INFORMATION FOR SEQ ID NO:29:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (v) FRAGMENT TYPE: N-terminal (ix) FEATURE:
(A) NAME/KEY: misc-feature
(B) LOCATION: 1
(D) OTHER INFORMATION: Xaa is pyroglutamic acid (xi) SEQUENCE DESCRIPTION: SEQ ID NO:29:

Xaa Tyr Asp Gly Glu Gly Leu Gly
1               5

(2) INFORMATION FOR SEQ ID NO:30:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (v) FRAGMENT TYPE: N-terminal (ix) FEATURE:
(A) NAME/KEY: misc-feature
(B) LOCATION: 1
(D) OTHER INFORMATION: Xaa is pyroglutamic acid (xi) SEQUENCE DESCRIPTION: SEQ ID NO:30:

Xaa Tyr Glu Gly Glu Gly Val Gly
1               5

(2) INFORMATION FOR SEQ ID NO:31:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (v) FRAGMENT TYPE: N-terminal (ix) FEATURE:
(A) NAME/KEY: misc-feature
(B) LOCATION: 1

(D) OTHER INFORMATION: Xaa is pyroglutamic acid (x i) SEQUENCE DESCRIPTION: SEQ ID NO:31:

Xaa Tyr Asp Gly Asp Gly Val Gly
1               5

(2) INFORMATION FOR SEQ ID NO:32:

(i) SEQUENCE CHARACTERISTICS:
        (A) LENGTH: 8 amino acids
        (B) TYPE: amino acid
        (C) STRANDEDNESS:
        (D) TOPOLOGY: linear (i i) MOLECULE TYPE: peptide (v) FRAGMENT TYPE: N-terminal (i x) FEATURE:
        (A) NAME/KEY: misc-feature
        (B) LOCATION: 1
        (D) OTHER INFORMATION: Xaa is pyroglutamic acid (x i) SEQUENCE DESCRIPTION: SEQ ID NO:32:

Xaa Tyr Glu Gly Asp Glu Val Gly
1               5

(2) INFORMATION FOR SEQ ID NO:33:

(i) SEQUENCE CHARACTERISTICS:
        (A) LENGTH: 8 amino acids
        (B) TYPE: amino acid
        (C) STRANDEDNESS:
        (D) TOPOLOGY: linear (i i) MOLECULE TYPE: peptide (v) FRAGMENT TYPE: N-terminal (i x) FEATURE:
        (A) NAME/KEY: misc-feature
        (B) LOCATION: 1
        (D) OTHER INFORMATION: Xaa is Glu converted (by
            autoclaving the peptide) to pyroglutamic acid (x i) SEQUENCE DESCRIPTION: SEQ ID NO:33:

Xaa Tyr Asp Gly Glu Gly Val Gly
1               5

(2) INFORMATION FOR SEQ ID NO:34:

(i) SEQUENCE CHARACTERISTICS:
        (A) LENGTH: 8 amino acids
        (B) TYPE: amino acid
        (C) STRANDEDNESS:
        (D) TOPOLOGY: linear (i i) MOLECULE TYPE: peptide (v) FRAGMENT TYPE: N-terminal (i x) FEATURE:
        (A) NAME/KEY: misc-feature
        (B) LOCATION: 1
        (D) OTHER INFORMATION: Xaa is pyroglutamic acid (i x) FEATURE:
        (A) NAME/KEY: misc-feature
        (B) LOCATION: 5
        (D) OTHER INFORMATION: Xaa is 2- aminoadipic acid (x i) SEQUENCE DESCRIPTION: SEQ ID NO:34:

Xaa Tyr Asp Gly Xaa Gly Val Gly 1               5

(2) INFORMATION FOR SEQ ID NO:35:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (xi) SEQUENCE DESCRIPTION: SEQ ID NO:35:

Xaa   Tyr   Asp   Gly   Glu   Gly   Val   Val
1                       5

(2) INFORMATION FOR SEQ ID NO:36:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (xi) SEQUENCE DESCRIPTION: SEQ ID NO:36:

Xaa   Phe   Asp   Gly   Glu   Gly   Val   Gly
1                       5

(2) INFORMATION FOR SEQ ID NO:37:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (xi) SEQUENCE DESCRIPTION: SEQ ID NO:37:

Xaa   Tyr   Asp   Val   Glu   Gly   Val   Gly
1                       5

(2) INFORMATION FOR SEQ ID NO:38:

(i) SEQUENCE CHARACTERISTICS:
        (A) LENGTH: 8 amino acids
        (B) TYPE: amino acid
        (C) STRANDEDNESS:
        (D) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( i x ) FEATURE:
    ( A ) NAME/KEY: misc-feature
    ( B ) LOCATION: 5
    ( D ) OTHER INFORMATION: Val is norvaline ( x i ) SEQUENCE DESCRIPTION: SEQ ID NO:38:

Xaa Tyr Asp Gly Val Gly Val Gly
1                 5

( 2 ) INFORMATION FOR SEQ ID NO:39:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:39:

Xaa Tyr Asp Gly Glu Gly Val Gly
1                 5

( 2 ) INFORMATION FOR SEQ ID NO:40:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( A ) NAME/KEY: misc-feature
    ( B ) LOCATION: 1
    ( D ) OTHER INFORMATION: Xaa is pyroglutamic acid ( x i ) SEQUENCE DESCRIPTION: SEQ ID NO:40:

Xaa Tyr Asp Gly Glu Gly Val Gly Leu
1                 5

( 2 ) INFORMATION FOR SEQ ID NO:41:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( x i ) SEQUENCE DESCRIPTION: SEQ ID NO:41:

Gly Gly Tyr Asp Gly Glu Gly Val Gly
1               5

(2) INFORMATION FOR SEQ ID NO:42:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (xi) SEQUENCE DESCRIPTION: SEQ ID NO:42:

Xaa Tyr Asp Gly Glu Gly Val Gly Gly Lys Leu
1               5                   10

(2) INFORMATION FOR SEQ ID NO:43:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (xi) SEQUENCE DESCRIPTION: SEQ ID NO:43:

Ser Tyr Asp Gly Glu Gly Val Gly
1               5

(2) INFORMATION FOR SEQ ID NO:44:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (ix) FEATURE:
        (A) NAME/KEY: misc-feature
        (B) LOCATION: 8
        (D) OTHER INFORMATION: Xaa is 1,2- diaminoacetaldehyde (xi) SEQUENCE DESCRIPTION: SEQ ID NO:44:

Xaa Tyr Asp Gly Glu Gly Val Xaa
1               5

(2) INFORMATION FOR SEQ ID NO:45:

(i) SEQUENCE CHARACTERISTICS:
        (A) LENGTH: 8 amino acids
        (B) TYPE: amino acid
        (C) STRANDEDNESS:
        (D) TOPOLOGY: linear ( i i ) MOLECULE TYPE: peptide ( v ) FRAGMENT TYPE: N-terminal ( x i ) SEQUENCE DESCRIPTION: SEQ ID NO:45:

Gly Val Gly Cys Gly Asp Tyr Gln
1               5

( 2 ) INFORMATION FOR SEQ ID NO:46:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:46:

Xaa Tyr Asp Gly Glu Val Val Gly
1               5

( 2 ) INFORMATION FOR SEQ ID NO:47:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:47:

Xaa Tyr Asp Gly Glu Gly Gly Gly
1               5

( 2 ) INFORMATION FOR SEQ ID NO:48:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:48:

Xaa Tyr Asp Gly Glu Gly Ala Gly
1               5

( 2 ) INFORMATION FOR SEQ ID NO:49:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:49:

Xaa Tyr Asp Gly Glu Gly Val Ala
1               5

( 2 ) INFORMATION FOR SEQ ID NO:50:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:50:

His Tyr Asp Gly Glu Gly Val Gly
1               5

( 2 ) INFORMATION FOR SEQ ID NO:51:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:51:

Pro Tyr Asp Gly Glu Gly Val Gly
1               5

( 2 ) INFORMATION FOR SEQ ID NO:52:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:52:

Xaa Tyr Asp Gly Glu Cys Gly Gly
1               5

( 2 ) INFORMATION FOR SEQ ID NO:53:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:53:

```
Xaa  Val  Gly  Glu  Gly  Asp  Tyr  Asn
1                   5
```

( 2 ) INFORMATION FOR SEQ ID NO:54:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:54:

```
Xaa  Tyr  Asp  Gly  Glu  Gly  Val  Pro
1                   5
```

( 2 ) INFORMATION FOR SEQ ID NO:55:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( x i ) SEQUENCE DESCRIPTION: SEQ ID NO:55:

```
Xaa  Tyr  Asp  Gly  Glu  Gly  Ile  Gly
1                   5
```

( 2 ) INFORMATION FOR SEQ ID NO:56:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide (v) FRAGMENT TYPE: N-terminal (ix) FEATURE:
    (A) NAME/KEY: misc-feature
    (B) LOCATION: 1
    (D) OTHER INFORMATION: Xaa is pyroglutamic acid (xi) SEQUENCE DESCRIPTION: SEQ ID NO:56:

```
Xaa  Tyr  Asp  Gly  Glu  Gly  Val  Cys
1                       5
```

(2) INFORMATION FOR SEQ ID NO:57:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is 4Hyp (xi) SEQUENCE DESCRIPTION: SEQ ID NO:57:

```
Xaa  Tyr  Asp  Gly  Glu  Gly  Val  Gly
1                       5
```

(2) INFORMATION FOR SEQ ID NO:58:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (ix) FEATURE:
        (A) NAME/KEY: misc-feature
        (B) LOCATION: 5
        (D) OTHER INFORMATION: Xaa is biotinylated Lys (xi) SEQUENCE DESCRIPTION: SEQ ID NO:58:

```
Xaa  Tyr  Asp  Gly  Xaa  Gly  Val  Gly
1                       5
```

(2) INFORMATION FOR SEQ ID NO:59:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1

(D) OTHER INFORMATION: Xaa is pyroglutamic acid (ix) FEATURE:
    (A) NAME/KEY: misc-feature
    (B) LOCATION: 5
    (D) OTHER INFORMATION: Xaa is biotinylated Cys (xi) SEQUENCE DESCRIPTION: SEQ ID NO:59:

```
Xaa  Tyr  Asp  Gly  Xaa  Gly  Val  Gly
1                   5
```

(2) INFORMATION FOR SEQ ID NO:60:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (ix) FEATURE:
        (A) NAME/KEY: misc-feature
        (B) LOCATION: 3
        (D) OTHER INFORMATION: Xaa is a negatively charged amino acid residue (ix) FEATURE:
        (A) NAME/KEY: misc-feature
        (B) LOCATION: 5
        (D) OTHER INFORMATION: Xaa is a negatively charged amino acid residue (xi) SEQUENCE DESCRIPTION: SEQ ID NO:60:

```
Xaa  Tyr  Xaa  Gly  Xaa  Gly  Val  Gly
1                   5
```

(2) INFORMATION FOR SEQ ID NO:61:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (ix) FEATURE:
        (A) NAME/KEY: misc-feature
        (B) LOCATION: 3
        (D) OTHER INFORMATION: Xaa is a negatively charged amino acid residue (ix) FEATURE:
        (A) NAME/KEY: misc-feature
        (B) LOCATION: 5
        (D) OTHER INFORMATION: Xaa is Pro, Trp, Nva, or His (xi) SEQUENCE DESCRIPTION: SEQ ID NO:61:

```
Xaa  Tyr  Xaa  Gly  Xaa  Gly  Val  Gly
1                   5
```

( 2 ) INFORMATION FOR SEQ ID NO:62:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( i x ) FEATURE:
        ( A ) NAME/KEY: misc-feature
        ( B ) LOCATION: 3
        ( D ) OTHER INFORMATION: Xaa is a negatively charged amino
            acid residue ( i x ) FEATURE:
        ( A ) NAME/KEY: misc-feature
        ( B ) LOCATION: 5
        ( D ) OTHER INFORMATION: Xaa is pyridinylalanine ( x i ) SEQUENCE DESCRIPTION: SEQ ID NO:62:

Xaa Tyr Xaa Gly Xaa Gly Val Gly
1                    5

( 2 ) INFORMATION FOR SEQ ID NO:63:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( i x ) FEATURE:
        ( A ) NAME/KEY: misc-feature
        ( B ) LOCATION: 3
        ( D ) OTHER INFORMATION: Xaa is a negatively charged amino
            acid residue ( i x ) FEATURE:
        ( A ) NAME/KEY: misc-feature
        ( B ) LOCATION: 5
        ( D ) OTHER INFORMATION: Xaa is an alpha-amino acid
            residue bearing a thiol group ( x i ) SEQUENCE DESCRIPTION: SEQ ID NO:63:

Xaa Tyr Xaa Gly Xaa Gly Val Gly
1                    5

( 2 ) INFORMATION FOR SEQ ID NO:64:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide (v) FRAGMENT TYPE: N-terminal (ix) FEATURE:
    (A) NAME/KEY: misc-feature
    (B) LOCATION: 1
    (D) OTHER INFORMATION: Xaa is pyroglutamic acid (ix) FEATURE:
    (A) NAME/KEY: misc-feature
    (B) LOCATION: 3
    (D) OTHER INFORMATION: Xaa is a negatively charged amino acid residue (ix) FEATURE:
    (A) NAME/KEY: misc-feature
    (B) LOCATION: 5
    (D) OTHER INFORMATION: Xaa is homocysteine (xi) SEQUENCE DESCRIPTION: SEQ ID NO:64:

Xaa Tyr Xaa Gly Xaa Gly Val Gly
1               5

(2) INFORMATION FOR SEQ ID NO:65:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (ix) FEATURE:
        (A) NAME/KEY: misc-feature
        (B) LOCATION: 3
        (D) OTHER INFORMATION: Xaa is a negatively charged amino acid residue (ix) FEATURE:
        (A) NAME/KEY: misc-feature
        (B) LOCATION: 5
        (D) OTHER INFORMATION: Xaa is an alpha-amino acid bearing a side chain amino or thiol group (xi) SEQUENCE DESCRIPTION: SEQ ID NO:65:

Xaa Tyr Xaa Gly Xaa Gly Val Gly
1               5

(2) INFORMATION FOR SEQ ID NO:66:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (ix) FEATURE:
        (A) NAME/KEY: misc-feature
        (B) LOCATION: 3

(D) OTHER INFORMATION: Xaa is a negatively charged amino
        acid residue (ix) FEATURE:
    (A) NAME/KEY: misc-feature
    (B) LOCATION: 5
    (D) OTHER INFORMATION: Xaa is glutamine (xi) SEQUENCE DESCRIPTION: SEQ ID NO:66:

Xaa  Tyr  Xaa  Gly  Xaa  Gly  Val  Gly
1                 5

(2) INFORMATION FOR SEQ ID NO:67:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (ix) FEATURE:
        (A) NAME/KEY: misc-feature
        (B) LOCATION: 3
        (D) OTHER INFORMATION: Xaa is a negatively charged amino
            acid residue (ix) FEATURE:
        (A) NAME/KEY: misc-feature
        (B) LOCATION: 5
        (D) OTHER INFORMATION: Xaa is aspartic acid (xi) SEQUENCE DESCRIPTION: SEQ ID NO:67:

Xaa  Tyr  Xaa  Gly  Xaa  Gly  Val  Gly
1                 5

(2) INFORMATION FOR SEQ ID NO:68:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: N-terminal (ix) FEATURE:
        (A) NAME/KEY: misc-feature
        (B) LOCATION: 1
        (D) OTHER INFORMATION: Xaa is pyroglutamic acid (ix) FEATURE:
        (A) NAME/KEY: misc-feature
        (B) LOCATION: 3
        (D) OTHER INFORMATION: Xaa is a negatively charged amino
            acid residue (ix) FEATURE:
        (A) NAME/KEY: misc-feature
        (B) LOCATION: 5
        (D) OTHER INFORMATION: Xaa is cysteic acid (xi) SEQUENCE DESCRIPTION: SEQ ID NO:68:

Xaa  Tyr  Xaa  Gly  Xaa  Gly  Val  Gly
1                 5

( 2 ) INFORMATION FOR SEQ ID NO:69:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( i x ) FEATURE:
        ( A ) NAME/KEY: misc-feature
        ( B ) LOCATION: 3
        ( D ) OTHER INFORMATION: Xaa is a negatively charged amino
            acid residue ( i x ) FEATURE:
        ( A ) NAME/KEY: misc-feature
        ( B ) LOCATION: 5
        ( D ) OTHER INFORMATION: Xaa is alpha- aminoadipic acid ( x i ) SEQUENCE DESCRIPTION: SEQ ID NO:69:

Xaa  Tyr  Xaa  Gly  Xaa  Gly  Val  Gly
1                        5

( 2 ) INFORMATION FOR SEQ ID NO:70:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( A ) NAME/KEY: misc-feature
        ( B ) LOCATION: 1
        ( D ) OTHER INFORMATION: Xaa is pyroglutamic acid ( i x ) FEATURE:
        ( A ) NAME/KEY: misc-feature
        ( B ) LOCATION: 3
        ( D ) OTHER INFORMATION: Xaa is a negatively charged amino
            acid residue ( i x ) FEATURE:
        ( A ) NAME/KEY: misc-feature
        ( B ) LOCATION: 5
        ( D ) OTHER INFORMATION: Xaa is proline ( x i ) SEQUENCE DESCRIPTION: SEQ ID NO:70:

Xaa  Tyr  Xaa  Gly  Xaa  Gly  Val  Gly
1                        5

( 2 ) INFORMATION FOR SEQ ID NO:71:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
                ( A ) NAME/KEY: misc-feature
                ( B ) LOCATION: 1
                ( D ) OTHER INFORMATION: Xaa is pyroglutamic acid ( i x ) FEATURE:
                ( A ) NAME/KEY: misc-feature
                ( B ) LOCATION: 3
                ( D ) OTHER INFORMATION: Xaa is a negatively charged amino
                        acid residue ( i x ) FEATURE:
                ( A ) NAME/KEY: misc-feature
                ( B ) LOCATION: 5
                ( D ) OTHER INFORMATION: Xaa is tryptophan ( x i ) SEQUENCE DESCRIPTION: SEQ ID NO:71:

Xaa   Tyr   Xaa   Gly   Xaa   Gly   Val   Gly
1                       5

( 2 ) INFORMATION FOR SEQ ID NO:72:

( i ) SEQUENCE CHARACTERISTICS:
                ( A ) LENGTH: 8 amino acids
                ( B ) TYPE: amino acid
                ( C ) STRANDEDNESS:
                ( D ) TOPOLOGY: linear ( i i ) MOLECULE TYPE: peptide ( v ) FRAGMENT TYPE: N-terminal ( i x ) FEATURE:
                ( A ) NAME/KEY: misc-feature
                ( B ) LOCATION: 1
                ( D ) OTHER INFORMATION: Xaa is pyroglutamic acid ( i x ) FEATURE:
                ( A ) NAME/KEY: misc-feature
                ( B ) LOCATION: 3
                ( D ) OTHER INFORMATION: Xaa is a negatively charged amino
                        acid residue ( i x ) FEATURE:
                ( A ) NAME/KEY: misc-feature
                ( B ) LOCATION: 5
                ( D ) OTHER INFORMATION: Xaa is norvaline ( x i ) SEQUENCE DESCRIPTION: SEQ ID NO:72:

Xaa   Tyr   Xaa   Gly   Xaa   Gly   Val   Gly
1                       5

( 2 ) INFORMATION FOR SEQ ID NO:73:

( i ) SEQUENCE CHARACTERISTICS:
                ( A ) LENGTH: 8 amino acids
                ( B ) TYPE: amino acid
                ( C ) STRANDEDNESS:
                ( D ) TOPOLOGY: linear ( i i ) MOLECULE TYPE: peptide ( v ) FRAGMENT TYPE: N-terminal ( i x ) FEATURE:
                ( A ) NAME/KEY: misc-feature
                ( B ) LOCATION: 1
                ( D ) OTHER INFORMATION: Xaa is pyroglutamic acid ( i x ) FEATURE:
                ( A ) NAME/KEY: misc-feature
                ( B ) LOCATION: 3
                ( D ) OTHER INFORMATION: Xaa is a negatively charged amino
                        acid residue

```
        ( i x ) FEATURE:
                ( A ) NAME/KEY: misc-feature
                ( B ) LOCATION: 5
                ( D ) OTHER INFORMATION: Xaa is histidine ( x i ) SEQUENCE DESCRIPTION: SEQ ID NO:73:

Xaa  Tyr  Xaa  Gly  Xaa  Gly  Val  Gly
        1                      5

( 2 ) INFORMATION FOR SEQ ID NO:74:

( i ) SEQUENCE CHARACTERISTICS:
                ( A ) LENGTH: 8 amino acids
                ( B ) TYPE: amino acid
                ( C ) STRANDEDNESS:
                ( D ) TOPOLOGY: linear ( i i ) MOLECULE TYPE: peptide ( v ) FRAGMENT TYPE: N-terminal ( i x ) FEATURE:
                ( A ) NAME/KEY: misc-feature
                ( B ) LOCATION: 1
                ( D ) OTHER INFORMATION: Xaa is pyroglutamic acid ( i x ) FEATURE:
                ( A ) NAME/KEY: misc-feature
                ( B ) LOCATION: 3
                ( D ) OTHER INFORMATION: Xaa is a negatively charged amino
                        acid residue ( i x ) FEATURE:
                ( A ) NAME/KEY: misc-feature
                ( B ) LOCATION: 5
                ( D ) OTHER INFORMATION: Xaa is histidine ( x i ) SEQUENCE DESCRIPTION: SEQ ID NO:74:

Xaa  Tyr  Xaa  Gly  Xaa  Gly  Val  Gly
        1                      5
```